(12) United States Patent
Hoggatt

(10) Patent No.: US 8,739,335 B1
(45) Date of Patent: Jun. 3, 2014

(54) TACTICAL STRETCHER AND CONVERTIBLE FIRST AID TABLE WITH DETACHABLE IV POLE

(76) Inventor: Johnathan D. Hoggatt, Ashland, VA (US)

( * ) Notice: Subject to any disclaimer, the term of this patent is extended or adjusted under 35 U.S.C. 154(b) by 113 days.

(21) Appl. No.: 13/550,742

(22) Filed: Jul. 17, 2012

(51) Int. Cl.
*A61G 1/013* (2006.01)
*A61G 1/048* (2006.01)
*A61G 1/056* (2006.01)

(52) U.S. Cl.
USPC ............. 5/626; 5/627; 5/620; 5/503.1; 5/658

(58) Field of Classification Search
USPC ............. 5/625–628, 110, 11, 503.1, 658, 620
See application file for complete search history.

(56) References Cited

U.S. PATENT DOCUMENTS

| | | | | |
|---|---|---|---|---|
| 1,305,388 A * | 6/1919 | Luria | ................................. | 5/626 |
| 2,367,167 A * | 1/1945 | Carpenter | .......................... | 5/627 |
| 2,640,996 A * | 6/1953 | Davis | .................................. | 5/8 |
| 3,007,180 A * | 11/1961 | Zaugg | ................................ | 5/625 |
| 3,426,367 A * | 2/1969 | Bradford | ........................... | 5/626 |
| 4,262,872 A * | 4/1981 | Kodet | ......................... | 248/311.3 |
| D301,021 S | 5/1989 | Dommerud | | |
| 4,893,323 A | 1/1990 | Cook, III | | |
| 5,005,230 A | 4/1991 | Congdon | | |
| 6,151,730 A * | 11/2000 | Weston | ............................. | 5/110 |
| 6,421,853 B1 | 7/2002 | Pecorelli et al. | | |
| 6,431,505 B2 * | 8/2002 | Chinn et al. | .................. | 248/121 |
| 6,907,632 B2 * | 6/2005 | Bourgraf, Jr. | ..................... | 5/627 |
| 7,150,465 B2 | 12/2006 | Darling, III | | |
| 8,443,472 B2 * | 5/2013 | Sherman et al. | ............... | 5/503.1 |

* cited by examiner

*Primary Examiner* — Michael Trettel
(74) *Attorney, Agent, or Firm* — Kyle A. Fletcher, Esq.

(57) ABSTRACT

The tactical stretcher and convertible first aid table with detachable IV pole includes a small and lightweight stretcher that is manually lifted with two sets of handles located at distal ends of the stretcher. The stretcher includes a plurality of straps to secure and immobilize a patient lying on the top surface of the stretcher. Two pairs of foldable legs rotate downwardly from a bottom surface to convert the stretcher to a first aid table. The foldable legs are limited to 90 degrees range of rotational movement from a horizontal position to a vertical position. An IV holder accessory is optionally provided, and secures itself to one of the handles. The IV holder includes a telescoping construction in order to adjust the elevation of an IV bag with respect to the stretcher.

11 Claims, 6 Drawing Sheets

TACTICAL STRETCHER AND CONVERTIBLE FIRST AID TABLE WITH DETACHABLE IV POLE

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

A. Field of the Invention

The present invention relates to the field of ambulatory stretchers, more specifically, a stretcher that can convert to a first aid table.

Emergency medical personnel often use stretchers that are manually lifted to carry a patient thereon. These types of stretchers are commonly associated in military operations where a soldier is wounded, and needs to be evacuated. Typically, manually-held stretchers can fold up for storage and or may include feet there under to enable placement upon the ground. However, these types of stretchers, when placed on the ground, leave the patient lying just a few inches above the ground surface. In situations where a patient is placed on the ground, emergency medical personnel may need to administer life-saving respective patient. In such a situation it would be desirable to the emergency medical personnel to have the patient at a waist level with respect to the emergency medical personnel as opposed to ankle height.

The device of the present application seeks to address this need by providing a highly mobile stretcher that is manually lifted to carry a patient thereon, and which converts to a first aid table to place the patient at an elevation above the ground surface suitable for access to the emergency medical personnel.

B. Discussion of the Prior Art

As will be discussed immediately below, no prior art discloses a manually lifted stretcher comprised of two sets of handles that extend at distal ends of said stretcher; wherein a plurality of straps are provided along the length of the stretcher in order to immobilize and secure a patient to a top surface of the stretcher; wherein opposing sets of foldable legs are included on the bottom surface of the stretcher, and rotate downwardly to a perpendicular orientation in order to convert said stretcher into a first aid table; wherein the foldable legs may rotate upwardly in order to convert said first aid table back to said stretcher; wherein an IV holder accessory is included and may optionally attach onto one of the handles, and include a telescoping body to adjust the elevation of an IV bag with respect to the stretcher; wherein a plurality of small feet extend downwardly from the stretcher in order to support the stretcher a few inches above the ground surface, and with the foldable legs fully retracted.

The Linares Patent Application Publication (U.S. Pub. No. 2010/0257673) discloses a combination support table and stretcher assembly. However, the legs rotate outwardly to form handles for use as a stretcher, and do not limit the range of rotation to 90 degrees.

The Cook, III Patent (U.S. Pat. No. 4,893,323) discloses a combination portable x-ray table and stretcher. However, the stretcher does not convert from a first aid table to a stretcher.

The Congdon Patent (U.S. Pat. No. 5,005,230) discloses a patient-transporting system including a combined transport stretcher/operating room table. However, the table is not a relatively small and lightweight stretcher that converts to a first aid table via legs that rotate downwardly from underneath the stretcher.

The Pecorelli et al. Patent (U.S. Pat. No. 6,121,853) discloses a stretcher for the cleansing of bedridden patients. However, the stretcher includes height adjustment means that are integrated into the wheeled cart portion of the stretcher.

The Darling, III Patent (U.S. Pat. No. 7,150,465) discloses a mission adaptable portable cart/utility table arrangement. However, the cart/utility table is a wheeled stretcher, which does not include legs that rotate downwardly to convert a manually lifted stretcher to a first aid table.

The Dommerud Patent (U.S. Pat. No. Des. 301,021) illustrates an ornamental design for a collapsible stretcher. However, the collapsible stretcher includes hardware to support the stretcher in an expanded state or a retracted state, and does not include legs that fold down to convert the stretcher to a first aid table.

While the above-described devices fulfill their respective and particular objects and requirements, they do not describe a manually lifted stretcher comprised of two sets of handles that extend at distal ends of said stretcher; wherein a plurality of straps are provided along the length of the stretcher in order to immobilize and secure a patient to a top surface of the stretcher; wherein opposing sets of foldable legs are included on the bottom surface of the stretcher, and rotate downwardly to a perpendicular orientation in order to convert said stretcher into a first aid table; wherein the foldable legs may rotate upwardly in order to convert said first aid table back to said stretcher; wherein an IV holder accessory is included and may optionally attach onto one of the handles, and include a telescoping body to adjust the elevation of an IV bag with respect to the stretcher; wherein a plurality of small feet extend downwardly from the stretcher in order to support the stretcher a few inches above the ground surface, and with the foldable legs fully retracted. In this regard, the tactical stretcher and convertible first aid table with detachable IV pole departs from the conventional concepts and designs of the prior art.

SUMMARY OF THE INVENTION

The tactical stretcher and convertible first aid table with detachable IV pole includes a small and lightweight stretcher that is manually lifted with two sets of handles located at distal ends of the stretcher. The stretcher includes a plurality of straps to secure and immobilize a patient lying on the top surface of the stretcher. Two pairs of foldable legs rotate downwardly from a bottom surface to convert the stretcher to a first aid table. The foldable legs are limited to 90 degrees range of rotational movement from a horizontal position to a vertical position. An IV holder accessory is optionally provided, and secures itself to one of the handles. The IV holder includes a telescoping construction in order to adjust the elevation of an IV bag with respect to the stretcher. The tactical stretcher may include a plurality of small feet that extend downwardly from the stretcher in order to support the stretcher a few inches above the ground surface when the foldable legs are fully retracted.

An object of the invention is to provide a stretcher that can convert from a manually lifted stretcher to a first aid table.

Another object of the invention is to provide a stretcher wherein two pairs of foldable legs are integrated into the construction of a bottom surface of the stretcher, and can rotate downwardly from a parallel orientation with respect to the stretcher to a perpendicular orientation with respect to the stretcher.

A further object of the invention is to convert the foldable legs from a horizontal orientation to a vertical orientation, and vice versa.

Another object of the invention is to include a pair of handles that extend on distal ends, which are grabbed by opposing persons to lift a patient lying thereon, and wherein straps are included to secure and immobilize the patient to the top surface of the stretcher.

Another object of the invention is to provide an IV holder accessory that can attach itself to one of the handles, and which can adjust the elevation of an IV bag with respect to the stretcher.

Another object of the invention is to enable the IV holder to rotate flat with respect to the handle/stretcher when not in use, and to rotate upwardly at an acute or right orientation with respect to the handle/stretcher when in use.

Another object of the invention is to include a plurality of small feet that are provided underneath the tactical stretch, which supports said stretcher a few inches above the ground surface when the foldable legs are not extended downwardly.

An even further object of the invention is to insure that the small feet do not interfere with the use of the foldable legs.

These together with additional objects, features and advantages of the tactical stretcher and convertible first aid table with detachable IV pole will be readily apparent to those of ordinary skill in the art upon reading the following detailed description of presently preferred, but nonetheless illustrative, embodiments of the tactical stretcher and convertible first aid table with detachable IV pole when taken in conjunction with the accompanying drawings.

In this respect, before explaining the current embodiments of the tactical stretcher and convertible first aid table with detachable IV pole in detail, it is to be understood that the tactical stretcher and convertible first aid table with detachable IV pole is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the tactical stretcher and convertible first aid table with detachable IV pole.

It is therefore important that the claims be regarded as including such equivalent construction insofar as they do not depart from the spirit and scope of the tactical stretcher and convertible first aid table with detachable IV pole. It is also to be understood that the phraseology and terminology employed herein are for purposes of description and should not be regarded as limiting.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Detailed reference will now be made to the preferred embodiment of the present invention, examples of which are illustrated in FIGS. 1-7. A tactical stretcher and convertible first aid table with detachable IV pole 100 (hereinafter invention) includes a stretcher body 101 from which two sets of handles 102 extend on distal ends, which are used to manually lift the invention 100. The handles 102 are separated by a width 102A, which defines the width of the stretcher body 101.

Figure 1:
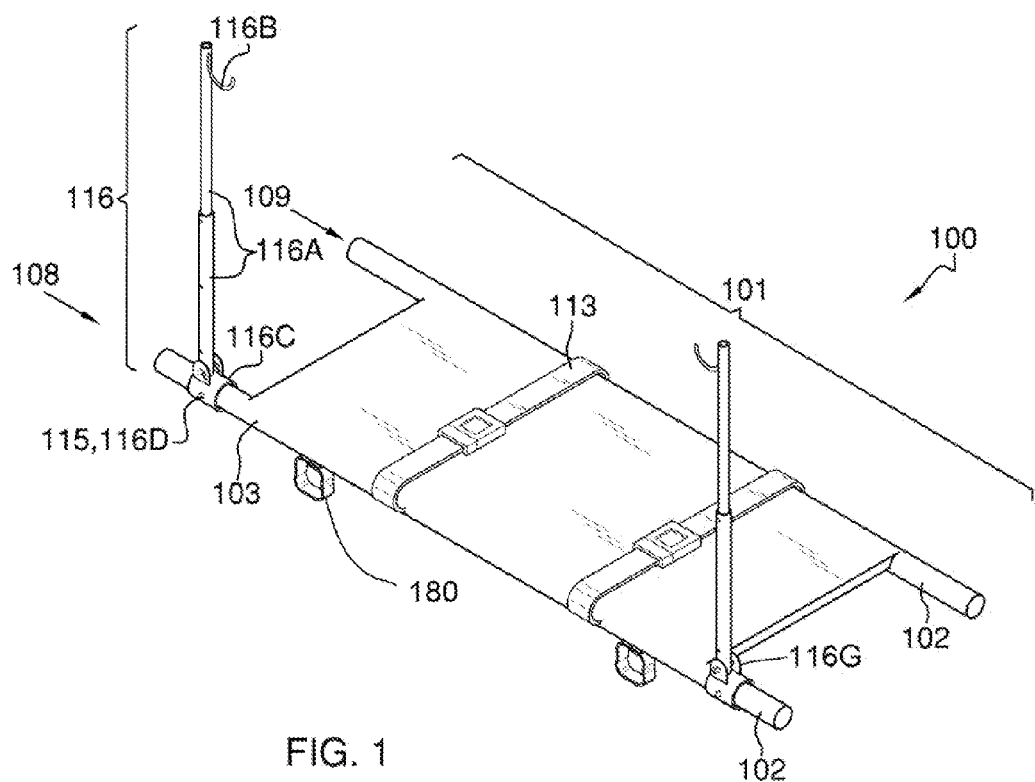
FIG. 1 illustrates a perspective view of the tactical stretcher and convertible first aid table with detachable IV pole by itself.
Figure 2:
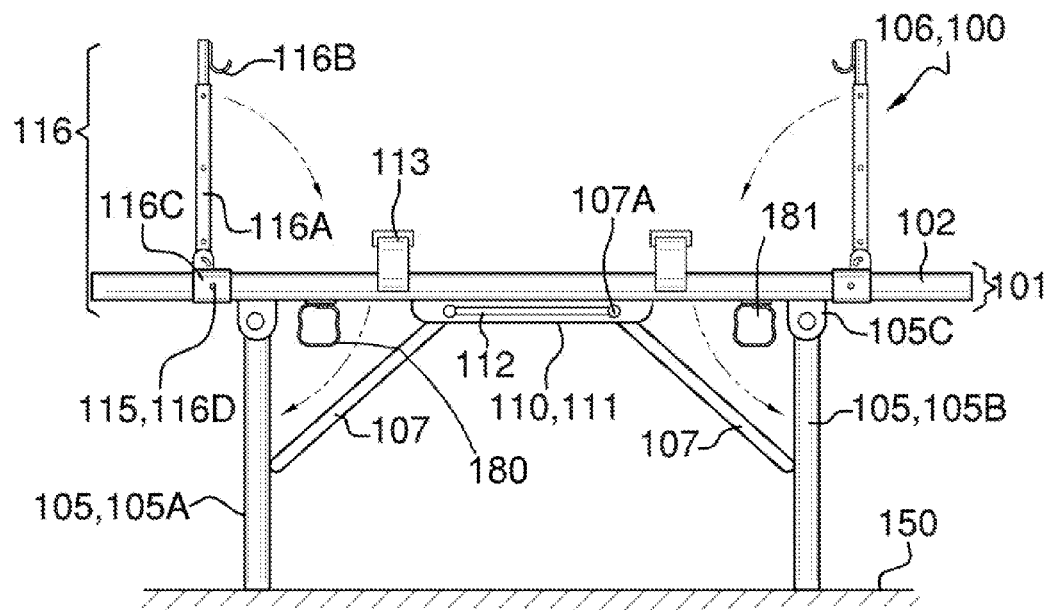
FIG. 2 illustrates a side view of the tactical stretcher in which the foldable legs are rotated down to form the first aid table, and also detailing the ability of the IV holder to rotate with respect to the handle/stretcher.
Figure 3:
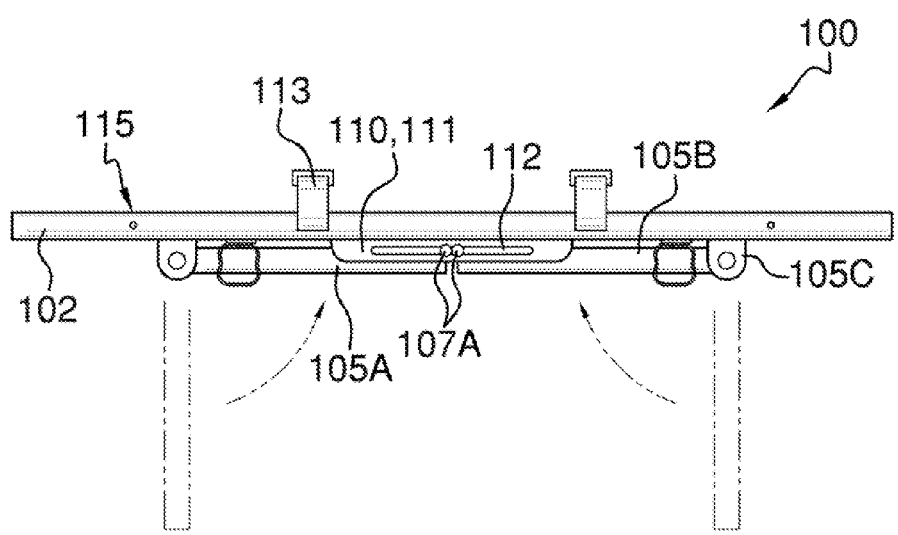
FIG. 3 illustrates a side view in which the foldable legs are rotated upwardly returning to the tactical stretcher, and further detailing the small feet that extend downwardly from the stretcher and which do not interfere with the rotational movement of the foldable legs there under.

The stretcher body 101 is further defined by a top surface 103 and a bottom surface 104. Two sets of foldable legs 105 are secured to the bottom surface 104, and rotate downwardly from a horizontal orientation to a vertical orientation in order to form the first aid table 106, as depicted in FIG. 2. The two sets of foldable legs 105 are further defined as a first set of foldable legs 105A and a second set of foldable legs 105B. The two sets of foldable legs 105 also attach to the bottom surface 104 at a pivot point 105C. The two sets of foldable legs 105 rotate clockwise or counterclockwise, and have a limited range of rotational movement of ninety degrees. The first set of foldable legs 105A rotates upwardly in a counterclockwise motion whereas the second set of foldable legs 105B rotates upwardly in a clockwise motion. That being said, the rotational movement of the first set of foldable legs 105A is always opposite that of the second set of foldable legs 105B.

Moreover, the two sets of foldable legs 105 each include a diagonal support 107 on either side of the stretcher body 101.

The stretcher body is further defined with a left side 108 and a right side 109. The diagonal supports 107 of the left side 108 slide along a left guide 110; whereas the diagonal supports 107x of the right side 109 slide along a right guide 110. The left guide 110 and the right guide 111 each include a slot 112 through which a sliding member 107A traverses.

As previously mentioned, the sets of foldable legs 105 rotate from a horizontal orientation to a vertical orientation with respect to a ground surface 150. That being said, the sets of foldable legs 105 rotate from a parallel orientation with respect to the stretcher body 101 (see FIG. 3) to a perpendicular orientation with respect to the stretcher body 101 (see FIG. 2). The range of motion of the foldable legs 105 from a horizontal to a vertical orientation is accomplished via the diagonal supports 107 and their respective sliding members 107A sliding back and forth along the left guide 110 and right guide 111. Moreover, the diagonal supports 107 are rotatable engaged with respect to the foldable legs 105, and provide the mechanical means necessary to limit the rotational movement of the foldable legs 105.

Figure 4:
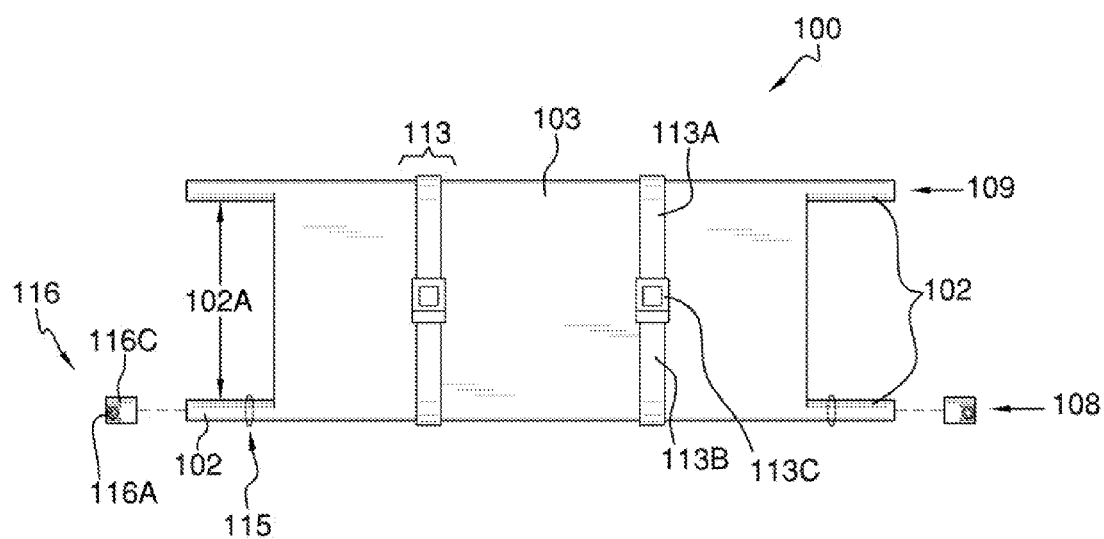
FIG. 4 illustrates a top view of the tactical stretcher and convertible first aid table in which the detachable IV pole is positioned adjacent two of the handles.
Figure 6:
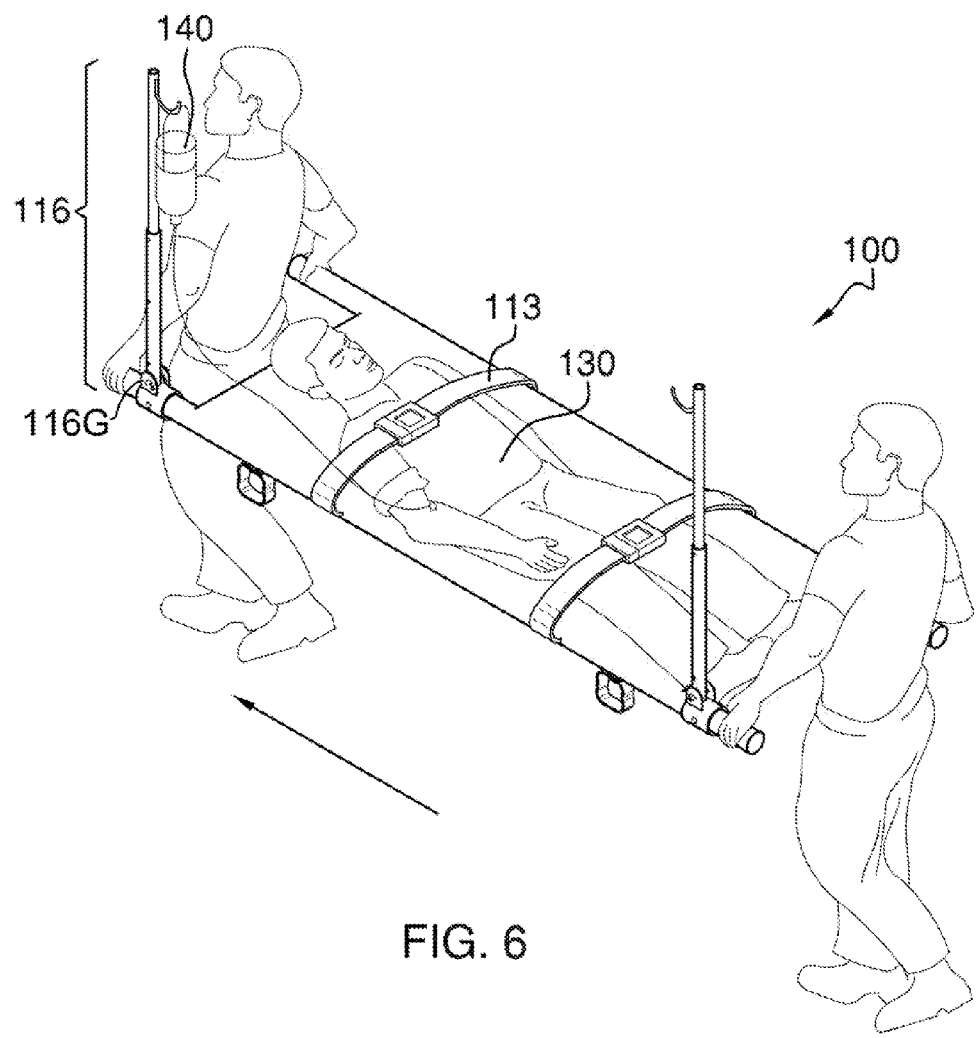
FIG. 6 illustrates a perspective view of the tactical stretcher in use as a stretcher in which a patient is secured thereon, and being transported via personnel.
Figure 7:
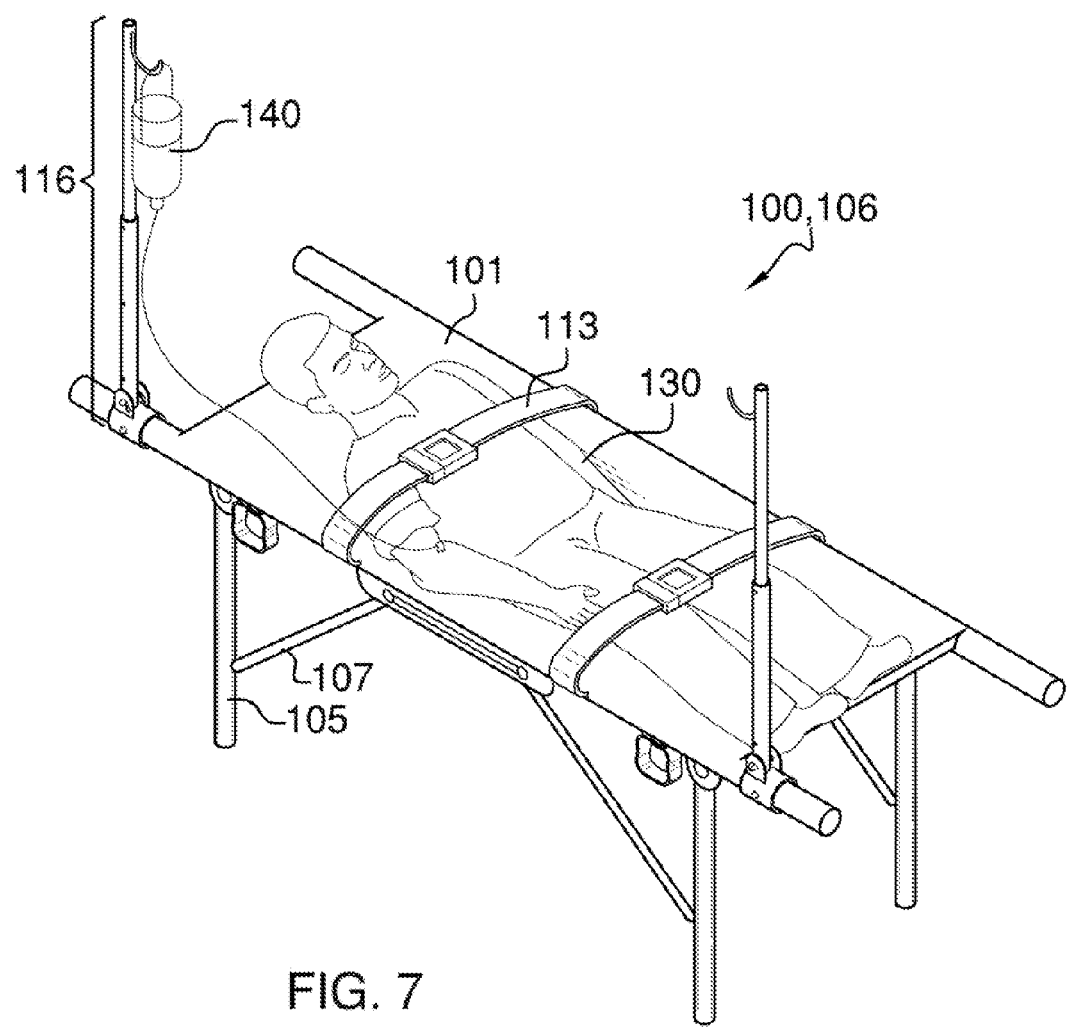
FIG. 7 illustrates a perspective view of the tactical stretcher in use as a first aid table with a patient secured thereon.

The stretcher body 101 also includes a plurality of straps 113 that are provided on the top surface 103 in order to immobilize and secure a patient 130 thereon (see FIGS. 6-7). The straps 113 are also available for use when the invention 100 is being used as a stretcher or as the first aid table. Referring to FIG. 4, the straps 113 are individually comprised of a first strap member 113A and a second strap member 113B that connect to one another via a buckle member 113C.

The invention 100 also includes a locking pin 115 that is located on one of the handles 102, which is used in connection it with an IV holder 116. The IV holder 116 includes a telescoping pole 116A that adjusts a hook 116B at a distal end in order to change an elevation of an IV 140 hung thereupon. The IV holder 116 also includes a handle bracket 116C that slides onto the handle 102 having the locking pin 115. The handle bracket 116C is a cylindrically-shaped member that includes a pin hole 116D to lock the handle bracket 116C with respect to the handle 102. Moreover, the locking pin 115 is a spring-loaded button 115 that is biased outwardly in order to lock the handle bracket 116 thereon.

It shall be noted that the telescoping pole 116A is rotatably engaged with respect to the handle bracket 116C as is depicted in FIG. 2 whereby the telescoping pole 116A can rotate from a perpendicular orientation with respect to the handles 102, to a parallel or acute orientation as denoted via the rotational arrow. The handle bracket 116C includes a pair of notched members 116G that extend upwardly therefrom, and which enable the telescoping pole 116A to pivot thereon.

The invention 100 may include a plurality of small feet 180 that extend downwardly from the bottom surface 104 of the stretcher body 101. Moreover, the small feet 180 are located between the handles 102 of each end of the stretcher body 101. The small feet 180 each have a square-shaped construction, whereby an opening 181 is formed therein. The small feet 180 extend downwardly from the stretcher body 101, and enable the invention 100 to rest a few inches above the ground surface 150. The small feet 180 are included as a useful means of resting the invention 100 just above the ground surface 150, and where the foldable legs 105 are fully retracted (see FIG. 3).

Figure 5:
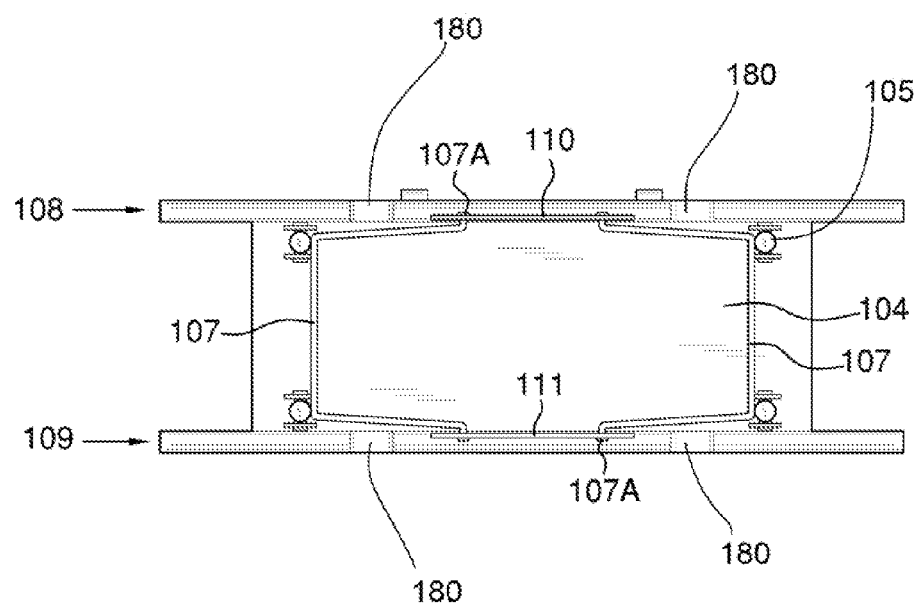
FIG. 5 illustrates a bottom view of the tactical stretcher and convertible first aid table, and detailing the foldable legs there under and adjacent with the small feet.

Referring to FIG. 5, it shall be noted that the small feet 180 do not interfere with the ability of the foldable legs 105 to rotate from a perpendicular to a parallel orientation with respect to the stretcher body 101, and vice versa.

With respect to the above description, it is to be realized that the optimum dimensional relationship for the various components of the invention 100, to include variations in size, materials, shape, form, function, and the manner of operation, assembly and use, are deemed readily apparent and obvious to one skilled in the art, and all equivalent relationships to those illustrated in the drawings and described in the specification are intended to be encompassed by the invention 100.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The invention claimed is:

1. A tactical stretcher and convertible first aid table comprising:
    a stretcher body from which two sets of foldable legs are attached and rotate from a horizontal orientation to a vertical orientation in order to convert from said tactical stretcher to said first aid table;
    wherein the stretcher body includes handles on distal ends to enable manual lift of the stretcher body with or without a patient lying thereon;
    wherein a plurality of small feet extend down from the bottom surface of the stretcher body, and provide an alternative means to support the stretcher body above the ground surface when the foldable legs are not in use;
    wherein the stretcher body is further defined with a top surface and a bottom surface; wherein the stretcher body is further defined with a left side and a right side; wherein at least one strap is provided, and extends across the top surface in order to secure said patient thereon;
    wherein the two sets of foldable legs attach to the bottom surface via pivot points;
    wherein the two sets of foldable legs are further defined as a first set of foldable legs and a second set of foldable legs;
    wherein the two sets of foldable legs each include a diagonal support on either side of the stretcher body; wherein the diagonal supports of the left side slide along a left guide; wherein the diagonal supports of the right side slide along a right guide; wherein the left guide and the right guide each include a slot through which a sliding member traverses.

2. The tactical stretcher and convertible first aid table as described in claim 1 wherein the handles are separated by a width on the stretcher body.

3. The tactical stretcher and convertible first aid table as described in claim 1 wherein the two sets of foldable legs rotate clockwise or counterclockwise, and have a limited range of rotational movement of ninety degrees.

4. The tactical stretcher and convertible first aid table as described in claim 3 wherein the first set of foldable legs rotates upwardly in a counterclockwise motion whereas the second set of foldable legs rotates upwardly in a clockwise motion.

5. The tactical stretcher and convertible first aid table as described in claim 1 wherein an IV holder attaches to one of the handles, and includes a hook at a distal end, which is adjusted via a telescoping pole in order to adjust an elevation of an IV bag hung thereon.

6. The tactical stretcher and convertible first aid table as described in claim 5 wherein the handle includes a locking pin that engages a pin hole located on a handle bracket in order to secure the IV holder thereon; wherein the telescoping pole is rotatable engaged with respect to the handle bracket.

7. A tactical stretcher and convertible first aid table comprising:
- a stretcher body from which two sets of foldable legs are attached and rotate from a horizontal orientation to a vertical orientation in order to convert from said tactical stretcher to said first aid table;
- wherein the stretcher body includes handles on distal ends to enable manual lift of the stretcher body with or without a patient lying thereon;
- wherein the stretcher body is further defined with a top surface and a bottom surface; wherein the stretcher body is further defined with a left side and a right side;
  - wherein at least one strap is provided, and extends across the top surface in order to secure said patient thereon;
- wherein the two sets of foldable legs attach to the bottom surface via pivot points;
- wherein the handles are separated by a width on the stretcher body;
- wherein the two sets of foldable legs are further defined as a first set of foldable legs and a second set of foldable legs;
- wherein the two sets of foldable legs rotate clockwise or counterclockwise, and have a limited range of rotational movement of ninety degrees;
- wherein the first set of foldable legs rotates upwardly in a counterclockwise motion whereas the second set of foldable legs rotates upwardly in a clockwise motion;
- wherein the two sets of foldable legs each include a diagonal support on either side of the stretcher body;
  - wherein the diagonal supports of the left side slide along a left guide; wherein the diagonal supports of the right side slide along a right guide; wherein the left guide and the right guide each include a slot through which a sliding member traverses.

8. The tactical stretcher and convertible first aid table as described in claim 7 wherein an IV holder attaches to one of the handles, and includes a hook at a distal end, which is adjusted via a telescoping pole in order to adjust an elevation of an IV bag hung thereon.

9. The tactical stretcher and convertible first aid table as described in claim 8 wherein the handle includes a locking pin that engages a pin hole located on a handle bracket in order to secure the IV holder thereon.

10. The tactical stretcher and convertible first aid table as described in claim 9 wherein the telescoping pole is rotatable engaged with respect to the handle bracket.

11. The tactical stretcher and convertible first aid table as described in claim 7 wherein a plurality of small feet extend down from the bottom surface of the stretcher body, and provide an alternative means to support the stretcher body above the ground surface when the foldable legs are not in use.

* * * * *